(12) United States Patent
Gorsek

(10) Patent No.: US 6,565,896 B1
(45) Date of Patent: May 20, 2003

(54) CHOLESTEROL TREATMENT FORMULATION

(75) Inventor: Wayne F. Gorsek, Boynton Beach, FL (US)

(73) Assignee: VitaCost.Com, Inc., Boynton Beach, FL (US)

( * ) Notice: Subject to any disclaimer, the term of this patent is extended or adjusted under 35 U.S.C. 154(b) by 0 days.

(21) Appl. No.: 10/187,614

(22) Filed: Jul. 3, 2002

(51) Int. Cl.⁷ .................. A01N 59/16; A01N 65/00; A61K 35/78
(52) U.S. Cl. .................. 424/655; 424/725; 424/766
(58) Field of Search ............... 424/725, 655, 424/766

(56) References Cited

U.S. PATENT DOCUMENTS

| | | | | |
|---|---|---|---|---|
| 6,113,949 A | * | 9/2000 | Brink | 424/602 |
| 6,197,832 B1 | * | 3/2001 | Sorkin | 514/729 |
| 6,365,186 B1 | * | 4/2002 | Huval et al. | 424/486 |

* cited by examiner

Primary Examiner—Herbert J. Lilling
(74) Attorney, Agent, or Firm—Hoffman, Wasson & Gitler, PC

(57) ABSTRACT

The invention relates to a composition which allows individuals to lower and maintain healthy cholesterol levels in the blood, and treat and prevent heart disease and strokes.

2 Claims, No Drawings

CHOLESTEROL TREATMENT FORMULATION

BACKGROUND OF THE INVENTION

The invention relates to a composition that contains the most potent combination of nutrients which help individuals support healthy cholesterol levels.

Cholesterol is a lipid substance that is used for many body processes. Low density lipoprotein, or LDL, is known as the bad cholesterol. High-density lipoprotein, or HDL, is known as the good cholesterol.

Cholesterol can build up on the inside of blood vessel walls. This results in arteriosclerosis, or hardening of the arteries. LDL cholesterol is the main source of build up on the blood vessel walls. HDL cholesterol carries cholesterol back to the liver and helps prevent build upon the blood vessel walls. It is an object of the present invention to provide an unique formulation which allows individuals to lower and maintain healthy cholesterol levels in the blood.

SUMMARY OF THE INVENTION

The key to the unique formulation is a combination of specific vitamins, minerals, herbs and nutrients. These essential components in the amounts provided uniquely contribute to a healthier cholesterol count in the bloodstream.

The formulation contains Gamma Oryzanol, Guglipids, Beta Sitosterol, Green Tea extract, Artichoke extract, Grape Seed extract, Chromium, Pantethine, Policosanol, as well as other healthy filler ingredients.

The formulation is preferably delivered in capsule form at 4 capsules per day.

DETAILED DESCRIPTION OF THE INVENTION

The present invention involves a composition for oral ingestion that contains Gamma Oryzanol, Guglipids, Beta Sitosterol, Green Tea Extract, Artichoke extract, Grape Seed extract, Chromium, Pantethine, Policosanol, as well as other healthy filler ingredients. More specifically, this formulated product is a cholesterol level management formulation. This formulation allows for maintenance of good HDL levels and reduction of bad LDL levels, treat and prevent heart disease and strokes which are the result of oxidized LDL cholesterol.

In order to secure the desired result the following essential components which all contribute to cholesterol maintenance are provided:

Gamma Oryzanol, approximately 300 mg, the component;

Gugulipids(standardized for 2.5% Guggul sterones (1.0 g)(30 mg–3,000 mg), (Approximately 1,000 mg (1.0 g)(100 mg–10,000 mg);

Beta Sitosterol (150 mg)(15 mg–1,500, mg);

Green tea Extract(Standardized 98% polyphenols, 80% catechins, 45% EGCG) are antioxidants which prevent the oxidation of LDL cholesterol (300 mg)(30 mg–3,000 mg);

Artichoke Extract(standardized for 5% Cynarine), (600 mg)(60 gm–6,000 mg);

Grape Seed Extract (ACTIVIN®), (200 mg) (20 mg–2,000 mg);

Chromium (chromium polynicotinate) (Chromemate) (400 mcg)(40 mcg–4,000 mcg);

Pantethine (450 mg)(45 mg–4,500 mg);

Poliucosanol (20 mg)(2 mg–2,000 mg)

In addition to the key components, other components such as kosher gelatin (capsules), magnesium stearate and silica and cellulose are included.

Although the invention has been described primarily in connection with special and preferred embodiments, it will be understood that it is capable of modification without departing from the scope of the invention. The following claims are intended to cover all variations, uses, or adaptations of the of the invention, following, in general the principles thereof and including such departures from the present disclosure as come within known or customary practice in the field to which the invention pertains, or as are obvious to persons skilled in the field.

What is claimed is:

1. A cholesterol treatment composition comprising an effective amount of:

Green Tea extract comprising standardized 98% polyphenols, 80% catechins; 45% EGCC;

Gamma Oryzanol;

Gugulipids;

Beta Sitosterol;

Artichoke extract standardized for 5% cynarine;

Grape Seed extract comprising by weight 54% proanthocyanidin dimer, 13% proanthocyanidin trimer, 7% proanthocyanidin tetramer, and 6% monomer;

Chromium;

Pantethine; and

Policosanol.

2. A cholesterol treatment composition as claimed in claim 1 comprising:

300 mg Green Tea extract;

300 mg Gamma Oryzanol;

1000 mg Gugulipids;

150 mg Beta Sitosterol;

600 mg Artichoke extract;

200 mg Grape Seed extract;

400 mcg Chromium;

450 mg Pantethine; and 20 mg Policosanol.

* * * * *